United States Patent
Chen et al.

(10) Patent No.: US 8,659,912 B2
(45) Date of Patent: Feb. 25, 2014

(54) SHIELDING DEVICE FOR SHIELDING AN ELECTRONIC COMPONENT

(75) Inventors: Singjang Chen, Beaverton, OR (US); Jonathan Benson, Oregon City, OR (US); Erica L. McCay, Salem, OR (US)

(73) Assignee: Biotronik SE & Co. KG, Berlin (DE)

( * ) Notice: Subject to any disclaimer, the term of this patent is extended or adjusted under 35 U.S.C. 154(b) by 371 days.

(21) Appl. No.: 13/083,865

(22) Filed: Apr. 11, 2011

(65) Prior Publication Data

US 2011/0272189 A1 Nov. 10, 2011

Related U.S. Application Data

(60) Provisional application No. 61/332,819, filed on May 10, 2010.

(51) Int. Cl.
*H05K 9/00* (2006.01)

(52) U.S. Cl.
USPC ........... 361/816; 361/800; 361/801; 361/818; 361/820

(58) Field of Classification Search
None
See application file for complete search history.

(56) References Cited

U.S. PATENT DOCUMENTS

| | | | |
|---|---|---|---|
| 5,838,551 A * | 11/1998 | Chan | 361/818 |
| 6,185,088 B1 | 2/2001 | Youker | |
| 6,625,040 B1 | 9/2003 | Tuttle | |
| 7,488,901 B2 | 2/2009 | Arnold | |
| 2004/0045158 A1 * | 3/2004 | Youker et al. | 29/830 |
| 2004/0154815 A1 * | 8/2004 | Gustafsson et al. | 174/35 R |
| 2004/0240191 A1 | 12/2004 | Arnold | |
| 2005/0051358 A1 * | 3/2005 | Kawamoto et al. | 174/260 |
| 2006/0266547 A1 * | 11/2006 | Koga | 174/255 |

FOREIGN PATENT DOCUMENTS

WO    WO 2008110533    9/2008

OTHER PUBLICATIONS

WO 2008/110533 English translation.*
European Search Report dated Sep. 28, 2011 (7 pages).

* cited by examiner

*Primary Examiner* — Tuan T Dinh
*Assistant Examiner* — Steven T Sawyer
(74) *Attorney, Agent, or Firm* — ARC IP Law, PC; Joseph J. Mayo (57) ABSTRACT

A shielding device for shielding an electronic component (102) to be mounted on a printed circuit board (132). The shielding device exhibiting a top shielding (110) and a bottom shielding (120; 140; 160; 180) separable from each other, wherein the top shielding includes an electrically and/or magnetically conductive material and the bottom shielding is multilayered. The bottom shielding exhibits at least one electrically and/or magnetically conductive metal sheet layer (122; 162; 164) embedded between at least two insulating layers (126; 124) and includes at least two electrically conductive transmission lines (172; 174; 176) for conducting electric current to the electronic component. The top shielding and the conductive metal sheet layer are electrically isolated from the electronic component. The bottom shielding integrated into the printed circuit board and the top shielding and the bottom shielding designed such when they are attached to each other, they completely envelope the electronic component.

19 Claims, 9 Drawing Sheets

SHIELDING DEVICE FOR SHIELDING AN ELECTRONIC COMPONENT

This application claims the benefit of U.S. Provisional Patent Application 61/332,819, filed 10 May 2010, the specification of which is hereby incorporated herein by reference.

BACKGROUND OF THE INVENTION

1. Field of the Invention

Embodiments of the invention relate to a shielding device for shielding an electronic component from magnetic and electric fields to be mounted on a printed circuit board, to a printed circuit board and to an electrically driven implant comprising a shielding device according to the invention. Furthermore, embodiments of the invention relate to a method of shielding an electronic component to be mounted on a printed circuit board. In particular, embodiments relate to an electrically driven implant, such as a defibrillator, comprising a shielding device for shielding a transformer.

2. Description of the Related Art

Shielding devices, such as shielding hoods, shielding caps or shielding cans for shielding electronic components, are principally known in the art. Such shielding devices primarily serve for reducing electromagnetic interference (EMI) between external electromagnetic radiation and electromagnetic radiation originating from the electronic component to be shielded. In particular, a shielding device can serve for preventing an external static magnetic field to enter the room sheathed by the shielding device.

The electronic component to be shielded can be an active electronic component, such as an integrated circuit, a power switch, a transistor or a passive electronic device, such as a resistor, a capacitor, an inductor or a transformer.

For reducing EMI, the known shielding devices are usually imposed over the electronic component, which is in most cases mounted to a printed circuit board. The known shielding devices are either fixed to the electronic component to be protected or to the printed circuit board. The latter case is, for instance, described in the U.S. Pat. No. 7,488,901.

Figure 1:
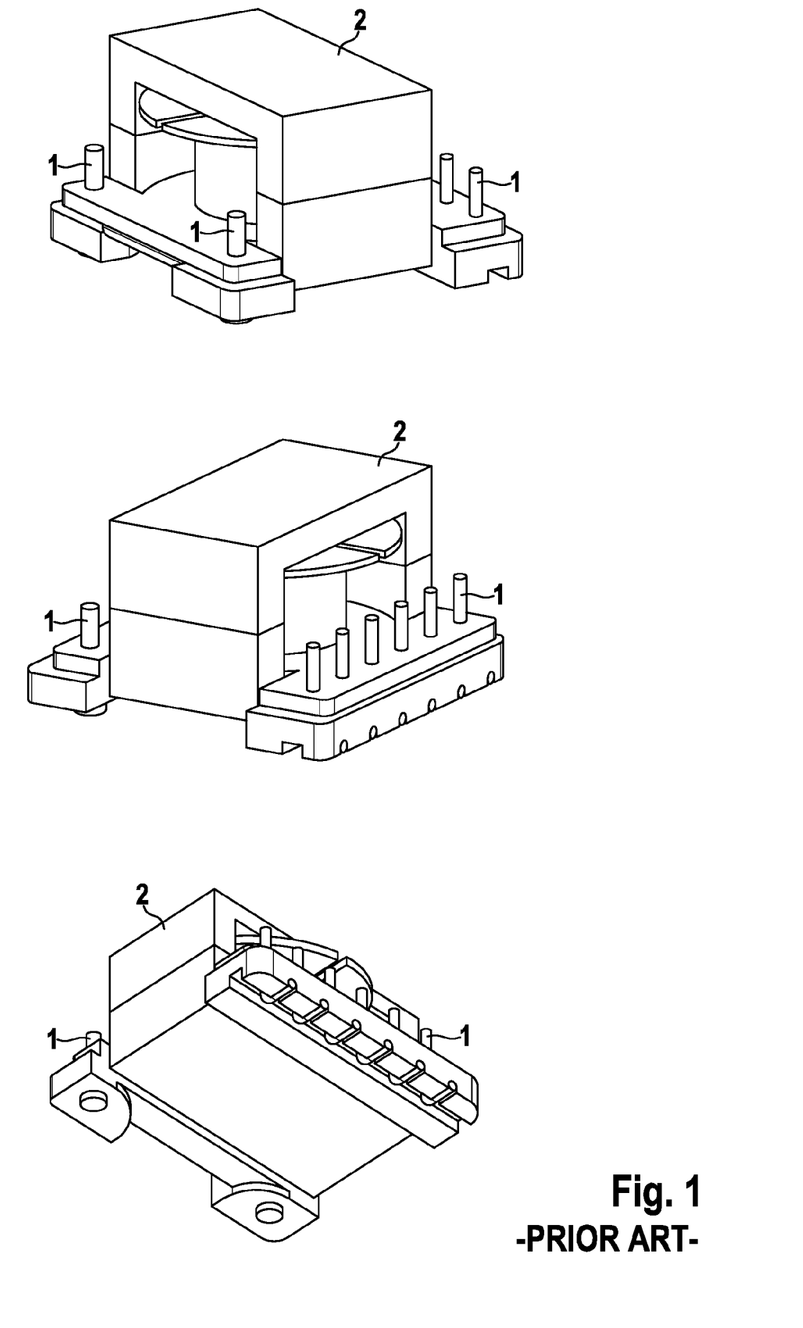
FIG. 1 shows schematically and exemplary a representation of a transformer according to the prior art.

FIG. 1 shows several views of an unshielded transformer as an example of a prior art electronic component. Such a transformer is, for instance, incorporated in an implantable defibrillator. If the transformer is operated in the presence of a strong external magnetic field, as can happen when an external programming device containing a strong permanent magnet is brought in close proximity to the defibrillator, a core of the transformer can saturate due to the strong external magnetic field. Such saturation can significantly reduce the operating efficiency of the transformer and, furthermore, can lead to a transformer failure.

A complete shielding of the transformer depicted in FIG. 1 is not possible with means of known shielding devices due to a plurality of attachment pins 1 which serve for attaching the transformer to a printed circuit board.

Figure 2A:
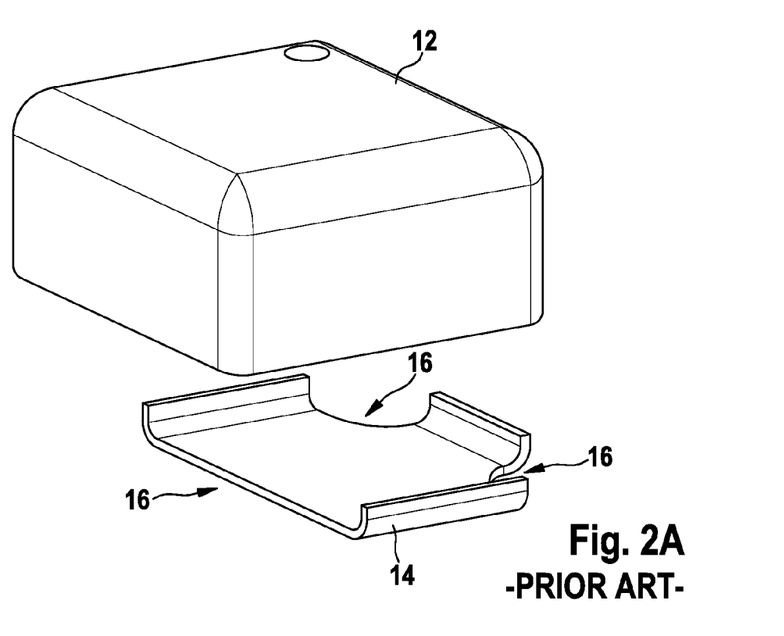
FIG. 2A shows schematically and exemplary a representation of a prior art shielding cap.

For shielding the transformer of FIG. 1, a shielding cap according to FIG. 2A is known. The known shielding cap comprises a top part 12 and a bottom part 14. Due to the attachment pins 1, the bottom part 14 of the known shielding cap exhibits cutouts 16 arranged at a side or, respectively, a corner. Because of these cutouts, the transformer 1 cannot be sheathed completely by the known shielding cap, resulting in an insufficient EMI protection. The gaps of the known shielding cap due to the cutouts 16 are also marked in FIG. 2C.

Figure 2B:
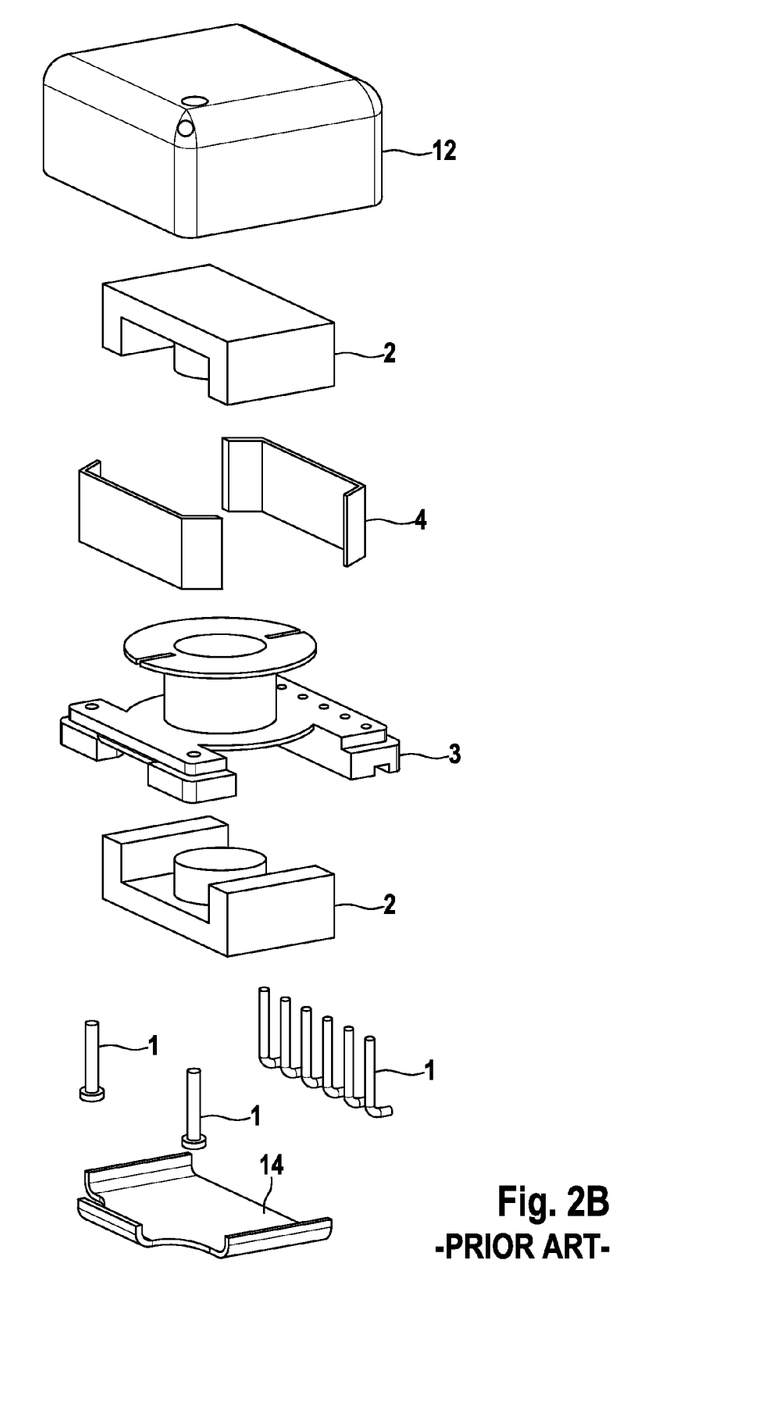
FIG. 2B shows schematically and exemplary a representation of a setup of a prior art transformer with a prior art shielding cap.
Figure 2C:
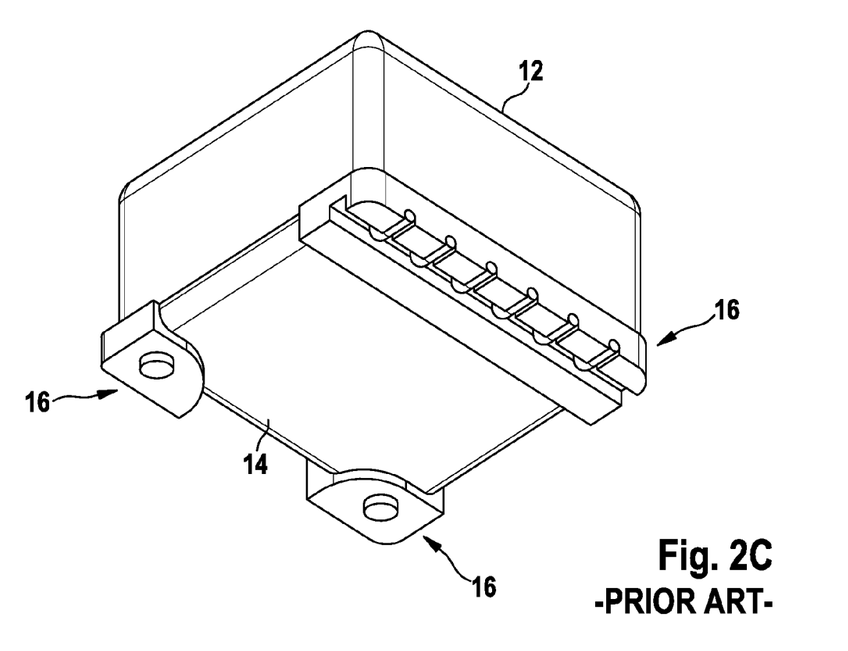
FIG. 2C shows schematically and exemplary a representation of a known shielding cap, shielding a known transformer.

In addition to an insufficient EMI protection, the known shielding cap of FIG. 2A furthermore constrains the mechanical robustness of the electronic component be shielded, as it additionally has to be fixed to the electronic component. As depicted in FIG. 2B, an electronic component can often be constructed of multiple single parts, such as, in case of a transformer, a magnetic core 2, a bobbin 3, an insulation wrapper 4, which are all mounted together on top of attachment pins 1. Not shown are the wires, which wind around the bobbin 3 and terminate onto the top of the attachment pins 1.

Due to limited space, the amount of attachment pins is also limited and a robust mechanical support for heavy components, as the transformer, cannot be ensured.

BRIEF SUMMARY OF THE INVENTION

It is, therefore, regarded as being an object of one or more embodiments of the invention to provide a shielding device with improved EMI protection. In particular, it is regarded as being an object of one or more embodiments of the invention to provide a shielding device with improved EMI protection for shielding a transformer used in an electrically driven implant.

According to a first aspect of one or more embodiments of the invention, the above stated object is achieved by providing a shielding device for shielding an electronic component to be mounted on a printed circuit board, wherein the shielding device exhibits a top shielding and a bottom shielding separable from each other and

- the top shielding comprises electrically and/or magnetically conductive material,
- the bottom shielding is multilayered, exhibiting at least one electrically and/or magnetically conductive metal sheet layer being embedded between at least two insulating layers and comprising at least two electrically conductive transmission lines for conducting electric current to the electronic component, wherein the top shielding and the conductive metal sheet layer are electrically isolated from the electronic component,
- the bottom shielding is integrated into the printed circuit board and
- the top shielding and the bottom shielding are designed such when they are attached to each other, they completely envelope the electronic component.

Due to the integration of the bottom shielding into the printed circuit board to which the electronic component is mounted, EMI protection of the electronic component is improved. The area, where no electrically and/or magnetically conductive material is present, is significantly reduced. An intrusion area for a magnetic flux of an external magnetic field is thus also reduced. For instance, a gap between the top shielding and the bottom shielding has a width which is substantially identical to a thickness of the insulating layer covering the electrically and/or magnetically conductive metal sheet layer, wherein the thickness is typically smaller than 100 μm.

As the electronic component is completely enveloped by the shielding device, operation of the electronic component is not disturbed by any external magnetic field. In particular, efficiency of an electronic component exhibiting a magnetic core is not affected by an external magnetic field since its influence, such as undesired changes in a magnetic flux flowing through the magnetic core, is substantially eliminated by the shielding device.

It shall be understood that within the scope of the description of one or more embodiments of the invention, the wording EMI protection is used for referencing a protection of all kinds of magnetic interference between an external magnetic field and operation of the electronic component to be shielded, such as protection from a static magnetic field and from an alternating magnetic field.

Electrical connection of the electronic component to be shielded to other electronic components on the printed circuit board is achieved by the at least two transmission lines. As the top shielding and the conductive metal sheet layer of the bottom shielding are electrically isolated from the electronic component, the electrically and/or magnetically conductive metal sheet layer does not or not necessarily serve as a ground plate or other transmission path for electric current to be guided through the printed circuit board. In particular, the shielding device does not require any grounding. This also reduces intrusion of undesired magnetic fields.

The integration of the bottom shielding into the printed circuit board results in a compact setup of the shielding device that is supportive for a mechanical robustness. In contrast to the known shielding cap, the bottom shielding does not require a complex manufacturing process, as cutouts, deflections or bends are not necessary. The electrically and/or magnetically conductive metal sheet layer of the bottom shielding is usually a plane layer simple to manufacture.

In the following, further embodiments of the shielding device of the first aspect of one or more embodiments of the invention are described. Additional features of these embodiments of the shielding device may be combined with each other and/or with optional features named above to form further embodiments, as far as they are not explicitly described as being alternative to each other.

Preferably, the top shielding is made of an electrically and/or magnetically conductive material. After imposing the top shielding over the electronic component, the top shielding is for instance glued to a top surface of the printed circuit board. The top shielding can be five sided.

For instance, the insulating layers are dielectric layers, such as polyimide layers.

The electronic component to be shielded is in most cases a coil, a transformer or another magnetic sensitive device. However, the electronic component can also be another passive component or an active component, such as a switch or an integrated circuit.

In a preferred embodiment, at least one edge of the electrically and/or magnetically conductive metal sheet layer is exposed such that when the top shielding and the bottom shielding are attached to each other, the top shielding contacts the at least one edge of the electrically and/or magnetically conductive metal sheet layer.

Due to the electrically and/or magnetically conductive contact between the top shielding and the bottom shielding, the EMI protection is furthermore improved. Preferably, the top shielding contacts the metal sheet layer of the bottom shielding such that the electronic component to be shielded is completely enveloped by an electrically and/or magnetically conductive material.

Another possibility to increase EMI protection offers transmissions lines through the bottom shielding which are each formed by at least two line sections that are displaced to each other such that they are not straight-lined.

In a particularly preferred embodiment, the multilayered bottom shielding comprises an upper insulating connection layer exhibiting a plurality of connection pads for electrically connecting the electronic component, a first electrically and/or magnetically conductive metal sheet layer arranged beneath the upper insulating connection layer, a middle insulating layer arranged beneath the first electrically and/or magnetically conductive metal sheet layer, a second electrically and/or magnetically conductive metal sheet layer arranged beneath the middle insulating layer and a lower insulating connection layer exhibiting a plurality of landing pads for electrically connecting the electronic component and arranged beneath the second electrically and/or magnetically conductive metal sheet layer, wherein each one of the plurality of landing pads is connectable to one of the plurality of connection pads through an electrically conductive transmission line.

This embodiment is particularly suitable for completely enveloping the electronic component to be shielded and for realizing a thorough EMI protection. Due to the two separated layers of magnetic shield material with offset passages for electrical connection, the EMI protection is furthermore improved. Each pad can be connected to a connection pad, but some pads may not be connected to anything and may simply serve to increase attachment area to the printed circuit board, thereby increasing attachment strength.

The upper insulating connection layer exhibiting the plurality of connection pads serves for electrically connecting the electronic component to be shielded. The connection pads are each electrically linked to at least one of the plurality of landing pads arranged at the lower insulating connection layer of the bottom shielding. Therefore, the electronic component to be shielded can be connected to other components of the printed circuit boards via the landing pads of the lower insulating connection layer. In particular, the transmission lines are electrically isolated from the first and the second electrically and/or magnetically conductive metal sheet layer.

For further improving the mechanical robustness of the bottom shielding, one of the connection pads is connected to more than one of the landing pads.

In the above described embodiment, the middle insulating layer preferably comprises a first insulating sublayer and a second insulating sublayer, the second insulating sublayer exhibiting a plurality of electrically conductive traces, each connecting the respective first and the second line sections of the plurality of transmission lines with each other, thereby realizing the displacement between them.

Due to this setup, the transition lines zigzag through the bottom shielding, thereby supporting EMI protection of the electronic component.

It is furthermore preferred that the second electrically and/or magnetically conductive metal sheet layer exhibits a larger surface area compared to the other layers of the bottom shielding such that the second electrically and/or magnetically conductive metal sheet layer has a protrusion area to which the top shielding can be mounted.

This embodiment has the advantage that the electrical contact between the top shielding and a metal sheet layer of the bottom shielding can easily be established. The usually five-sided top shielding is imposed over the electric component and mounted to the protrusion area of the second electrically and/or magnetically conductive metal sheet layer.

Usually, the layers of the bottom shielding are of rectangular shape such that the protrusion are of the second electrically and/or magnetically conductive metal sheet layer forms a frame of a rectangular shape.

In a particularly preferred embodiment, the top shielding and the bottom shielding are adapted to shield the electronic component from static magnetic fields. For instance, the shielding device is adapted to prevent an external magnetic field exhibiting a flux of 500 Gauss (Gs; 1 Gs=$10^{-4}$ Tesla) or higher from intruding the room sheathed by the shielding device.

As already elaborated above, some electronic components, especially those employed in an implant, do not only have to be protected from high frequency magnetic or electric fields but especially from static magnetic fields. Such a static magnetic field can, for instance, occur if a device comprising a permanent magnet is approaching the electronic component to be shielded.

For instance, the metal sheet layer/layers of the bottom shielding and the top shielding are made of a soft magnetic material, such as permalloy, cold-rolled steal or mu-metal. For ensuring protection against static magnetic fields, it is preferred in all embodiments that the material of the metal sheet layer/layers is a Fe- and/or Ni-based magnetic material.

Preferably, each layer of the multilayered bottom shielding is thin, for instance, the metal sheet layer/layers has/have a thickness between 250 μm and 1 mm, but both thinner or thicker layers could be used.

According to a second aspect of the present invention, a printed circuit board is proposed, wherein a shielding device according to the first aspect of one or more embodiments of the invention is assembled to the printed circuit board.

As the bottom shielding is integrated into the printed circuit board, the assembly of the printed circuit board and an electronic component shielded by the shielding device of one or more embodiments of the invention results in a low complexity and robust setup.

According to a third aspect of one or more embodiments of the invention, an electrically driven implant is proposed, the electrically driven implant comprising a shielding device according to the first aspect of one or more embodiments of the invention. The shielding device is in particular adapted to shield a transformer used in a defibrillator.

According to a fourth aspect of one or more embodiments of the invention, a method of shielding an electronic component to be mounted on a first circuit board is proposed. The method of the fourth aspect of one or more embodiments of the invention comprises steps of
   providing a shielding device according to the first aspect of the present invention,
   attaching the electronic component to an upper insulating layer of a bottom shielding of the shielding device,
   establishing an electronic connection between the electronic component and transmission lines of the shielding device,
   imposing a top shielding of the shielding device over the electronic component, thereby ensuring that the top shielding is in contact with a metal sheet layer/metal sheet layers of the bottom shielding,
   attaching the top shielding to the bottom shielding.

The method of the fourth aspect of one or more embodiments of the invention shares the advantages of the shielding device of the first aspect of one or more embodiments of the invention. The electronic component is, for instance, attached to the top surface of the bottom shielding through a soldering process or by welding or with conductively filled adhesives.

BRIEF DESCRIPTION OF THE DRAWINGS

The above and other aspects, features and advantages of one or more embodiments of the invention will be more apparent from the following more particular description thereof, presented in conjunction with the following drawings wherein.

DETAILED DESCRIPTION OF THE INVENTION

To simplify matters, none of the figures show the wires that wind around the bobbin 3 and terminate onto the top of the attachment pins 1. One skilled in the art will readily understand the drawings as including the wires.

FIGS. 1, 2A and 2B are described in the Description of the Related Art section above.

Figure 3A:
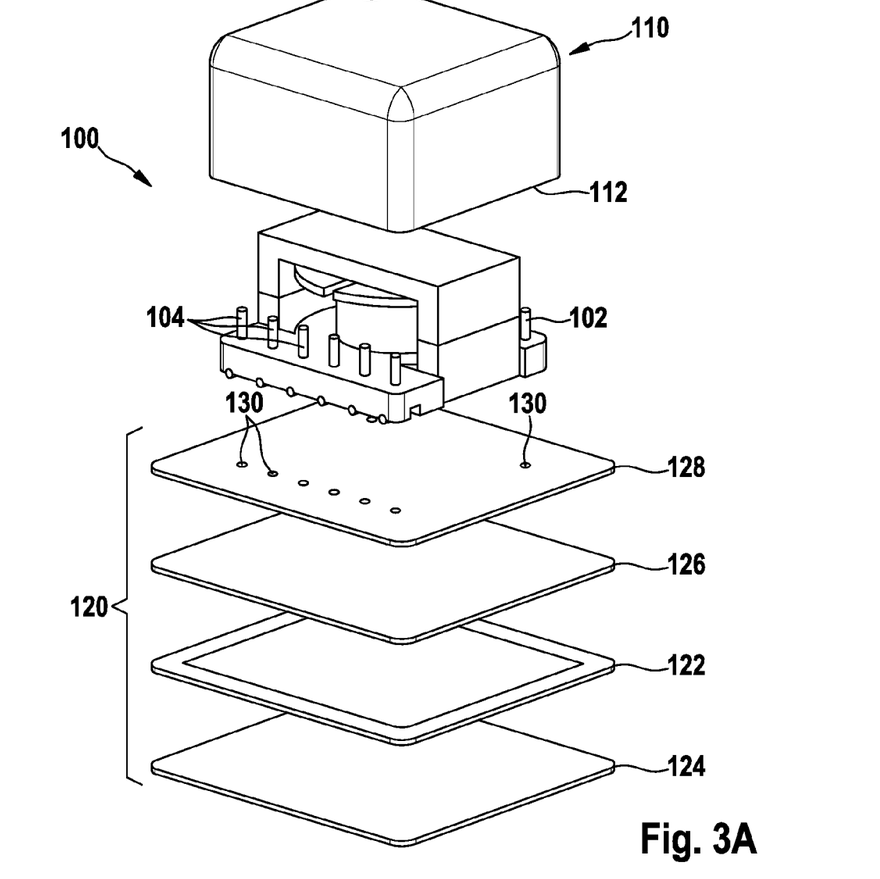
FIG. 3A shows schematically and exemplary a representation of a setup of a first embodiment of the shielding device of the present invention.

FIG. 3A schematically and exemplary shows a representation of a first embodiment 100 of the shielding device. The first embodiment 100 comprises a top shielding 110 and a bottom shielding 120 and serves for shielding an electronic component 102 which is, for instance, a transformer as shown in FIG. 3A. It shall be understood that the electronic component 102 is not part of the shielding device 100.

The top shielding 110 is five-sided and is made of an electrical conductive material, such as a permalloy.

The bottom shielding 120 is multilayered and exhibits an electrically and/or magnetically conductive metal sheet layer 122 which is embedded between two insulating layers 124 and 126. The middle insulating layer 126 is covered by an upper insulating layer 128. The insulating layers are made of a very thin insulating film, such as 25 μm thick polyimide.

The upper insulating layer 128 comprises a plurality of connection pads 130 for electrically connecting the electronic component 102. Each one of the plurality of connection pads 130 is connected to a transmission line arranged at the bottom of the upper insulating layer 128 (not visible in FIG. 3A) with means of through-vias. These transmission lines are used to conduct current from the electronic component to other components of the printed circuit board or vice versa. The connection pads 130 of the first embodiment 100 are, for instance, soldering eyes.

The middle insulating layer 126 isolates the transmission lines arranged at the bottom of the upper insulating layer 128 from the electrically and/or magnetically conductive metal sheet layer 122.

The electrically and/or magnetically conductive metal sheet layer 122 is embedded in a plate and made of a suitable magnetic shield material, such as cold-rolled steel or mu-metal.

The surface area of each layer of the multilayered bottom shield 120 is larger than the bottom surface of the electronic component 102 to be shielded.

For instance, the electronic component 102 is assembled to the upper insulating layer 128 by soldering, welding or by brazing on of a plurality of attachment pins 104 of the electronic component 102 to one of the plurality of connection pads 130. Additionally, non-conductive adhesive can be used to secure the electronic component 102 to the upper insulating layer 128.

The top shielding 110 is placed over the electronic component 102 such that bottom edges 112 of the top shielding 110 contact the upper insulating layer 128. Therefore, a shielding gap between the top shielding 110 and the metal sheet layer 122 is reduced to a thickness of the upper insulating layer 128 and the middle insulating layer 126, which is usually smaller than 100 µm. The top shielding 110 can be attached to the upper insulating layer 128 for instance by soldering or an adhesive or clamps.

Figure 3B:
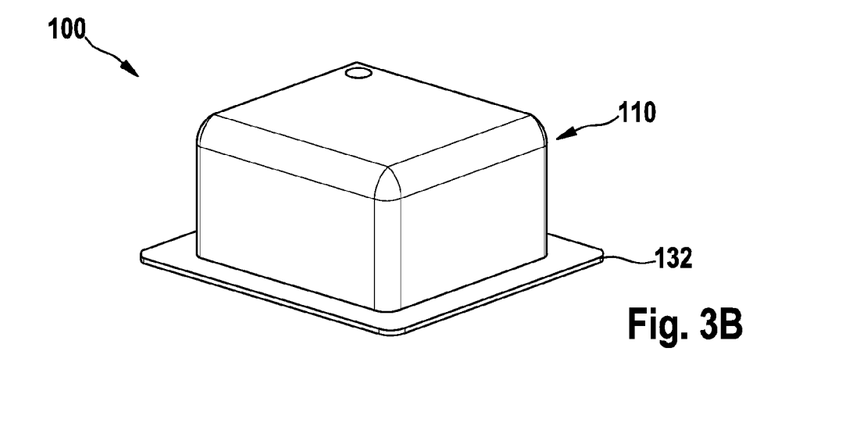
FIG. 3B shows schematically and exemplary a representation of the first embodiment of the shielding device arranged on a printed circuit board.

FIG. 3B shows exemplary and schematically a representation of the first embodiment 100 of the shielding device assembled to a printed circuit board 132, wherein the bottom shielding 120 is integrated into that printed circuit board 132.

Figure 4A:
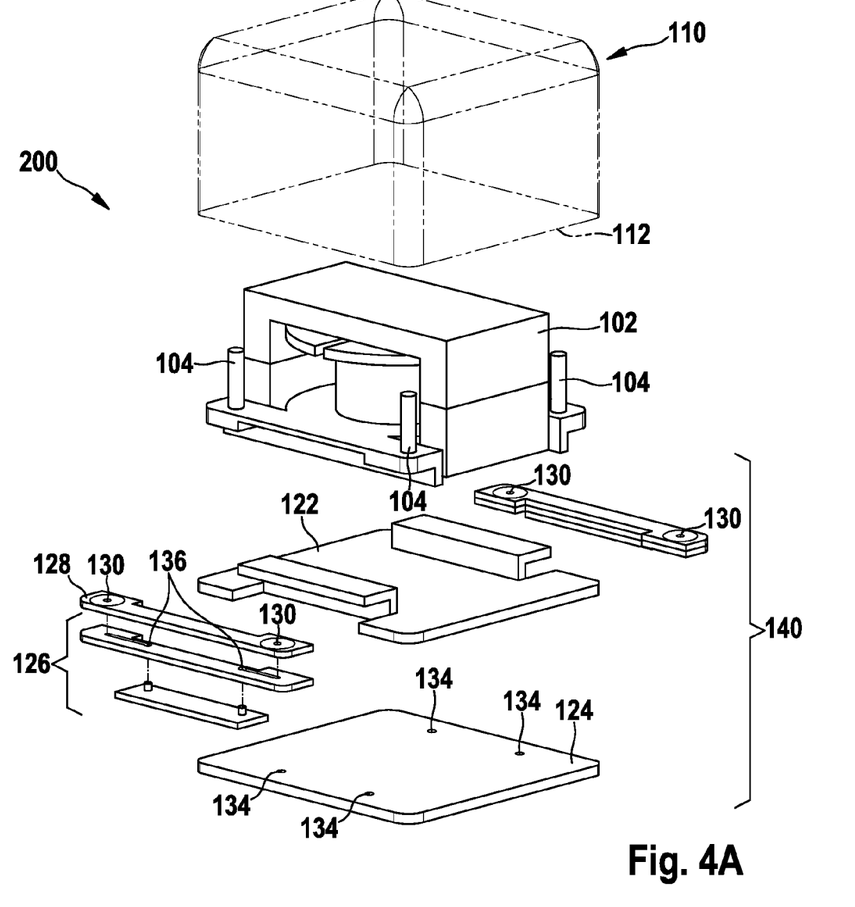
FIG. 4A shows schematically and exemplary a representation of a setup of a second embodiment of the shielding device of the present invention.

FIG. 4A shows schematically and exemplary a second embodiment 200 of the shielding device. As the first embodiment 100, the second embodiment 200 comprises a five-sided top shielding 110. However, the second embodiment 200 has a different bottom shielding 140. In this embodiment, the bottom shielding 140 is also multilayered, but the upper insulating layer 128 and the middle insulating layer 126 are formed as insulating bars.

Four attachment pins 104 of the electronic component 102 are each soldered to one of the plurality of connection pads 130 arranged at the upper insulating layer 128. Each one of the connection pads 130 is connected to one of a plurality of landing pads 134 arranged at the lower insulating layer 124. On two sides, the electrically and/or magnetically conductive metal sheet layer 122 is bent up forming an angle bracket such that the middle insulating layer 126 and the upper insulating layer 128 can be arranged in these angle brackets. The bottom shielding 140 is setup such that the electronic component 102 and the metal sheet layer 122 are electrically isolated from each other.

Each one of a plurality of transmission lines 136 connecting the plurality of connection pads 130 with the plurality of landing pads 134 is formed by two line sections that are displaced to each other such that each one of the transmission lines 136 is not straight-lined. This can be taken from FIG. 4A, as the landing pads 134 are arranged towards a respective side center, whereas the connection pads 130 are arranged at a corner of the upper insulating layer 128. The middle insulating layer comprises a plurality of conducting traces for connecting the respective first and the second line sections of the plurality of transmission lines 136, thereby realizing the displacement between them. The bottom side of insulating layer 124 has a plurality of pads for electrically connecting the electronic device to other devices, and for mounting to a printed circuit board.

Figure 4B:
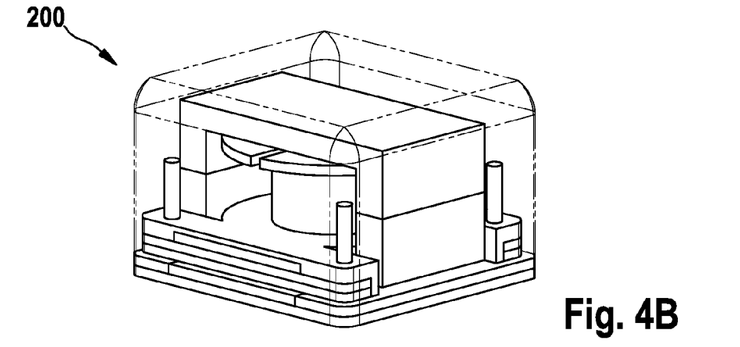
FIG. 4B shows schematically and exemplary a representation of the second embodiment of the shielding device shielding a transformer.

FIG. 4B schematically and exemplary shows a representation of an assembled second embodiment 200 of the shielding device shielding a transformer.

Figure 5A:
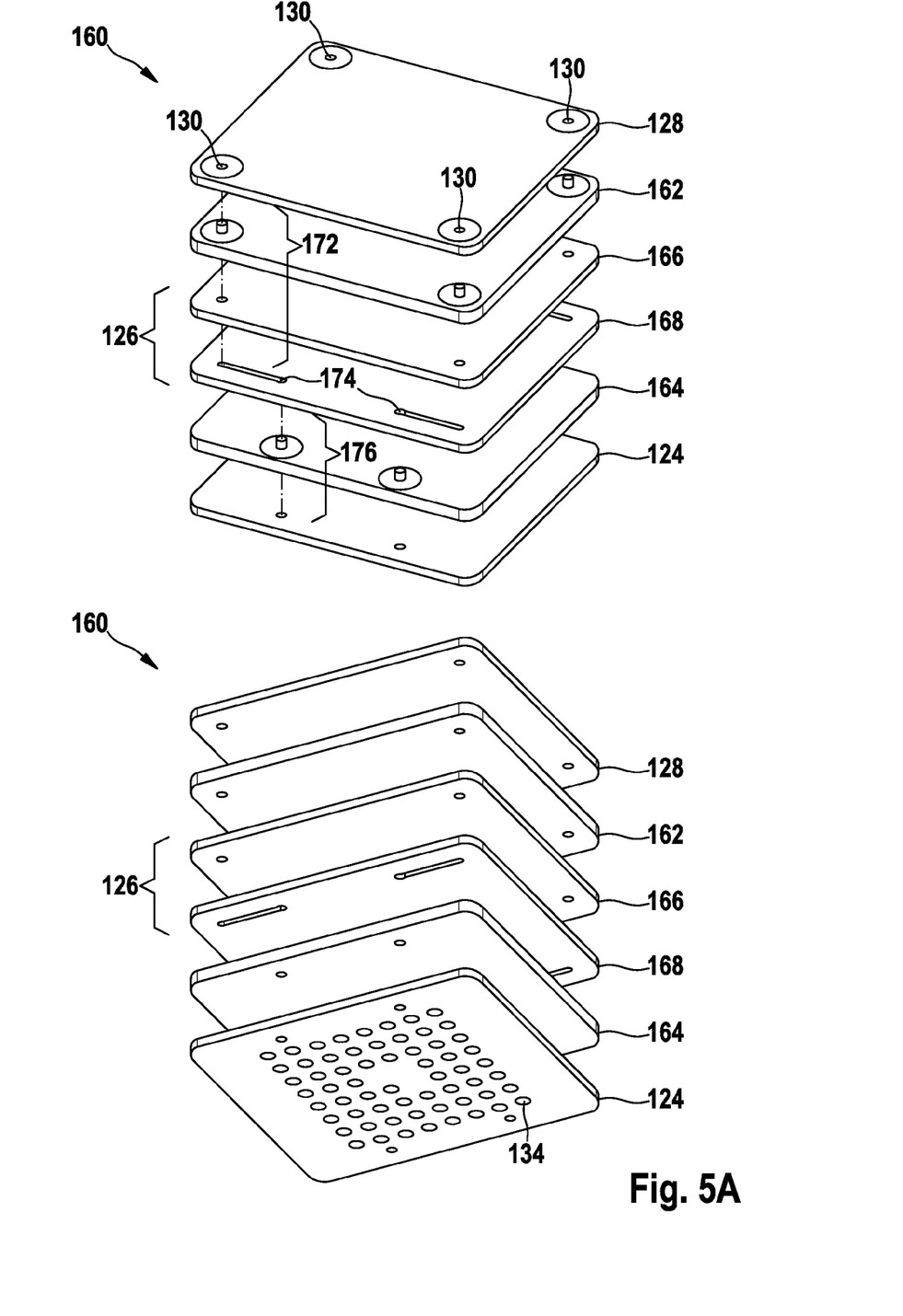
FIG. 5A shows schematically and exemplary a top view and a bottom view of a setup of a multilayered bottom shielding of a third embodiment of the shielding device of the present invention.

FIG. 5A shows exemplary and schematically a top view (left side), and a bottom view (right side) of a bottom shielding of a third embodiment 160 of the shielding device. The bottom shielding 160 of the third embodiment of the shielding device comprises an upper insulating layer 128 exhibiting the plurality of connection pads 130 for electrically connecting an electronic component. A first electrically and/or magnetically conductive metal sheet layer 162 is arranged beneath the upper insulating layer 128. A middle insulating layer arranged between the first metal sheet layer 162 and a second metal sheet layer 164 comprises a first insulating sublayer 166 and a second insulating sublayer 168. The second insulating sublayer 168 exhibits a plurality of electrically conductive traces 174, which connect a first line section 172 and a second line section 176 to each other, thereby realizing the displacement between them.

The first line section 172, the conductive trace 174 and the second line section 176 form a transmission line which connects one of the plurality of connection pads 130 to one or more of the plurality of landing pads 134. The first metal sheet layer 162 and the second metal sheet layer 164 are electrically isolated from the electrically conductive transmission line. The transmission line is for instance made of copper.

Figure 5B:
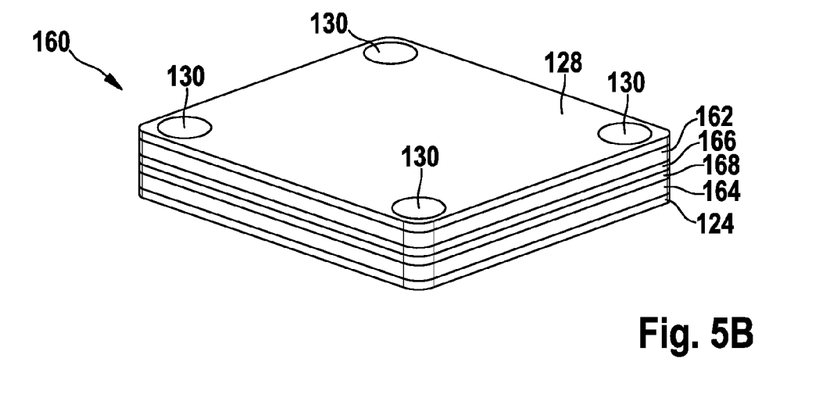
FIG. 5B shows schematically and exemplary a representation of the multilayered bottom shielding of the third embodiment of the shielding device of the present invention.

FIG. 5B shows an assembled view of the bottom shielding 160 of the third embodiment of the shielding device.

Figure 6A:
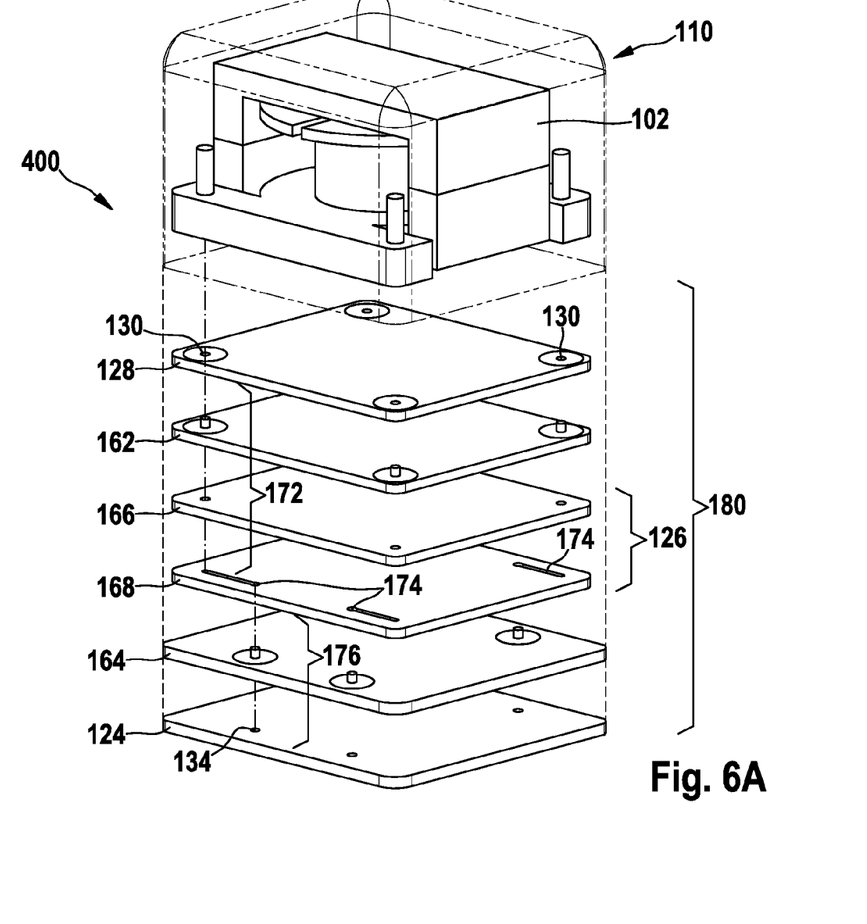
FIG. 6A shows schematically and exemplary a representation of setup of a fourth embodiment of the shielding device of the present invention.
Figure 6B:
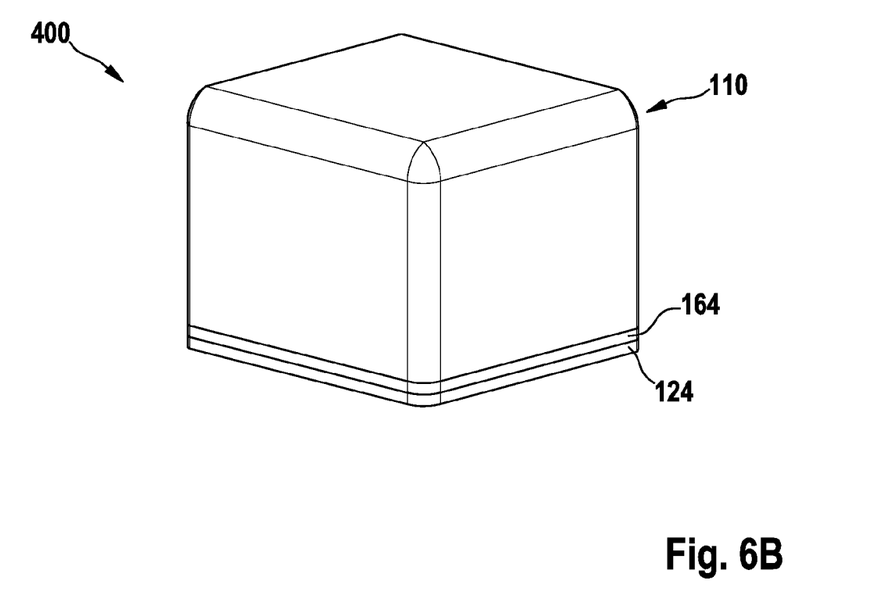
FIG. 6B shows schematically and exemplary a second representation of the fourth embodiment of the shielding device of the present invention.

FIG. 6A shows schematically and exemplary a representation of a fourth embodiment 400 of the shielding device. The fourth embodiment 400 also comprises a top shielding 110 and a bottom shielding 180. The bottom shielding 180 of the fourth embodiment 400 only differs slightly from the bottom shielding 160 of the third embodiment of the shielding device. The most significant difference is that the second metal sheet layer 164 and the lower insulating layer 164 both exhibit a larger surface area compared to the other layers of the bottom shielding 180. This larger surface area results in a protrusion area to which the top shielding 110 can be mounted, as schematically and exemplary shown in FIG. 6B.

Figure 7:
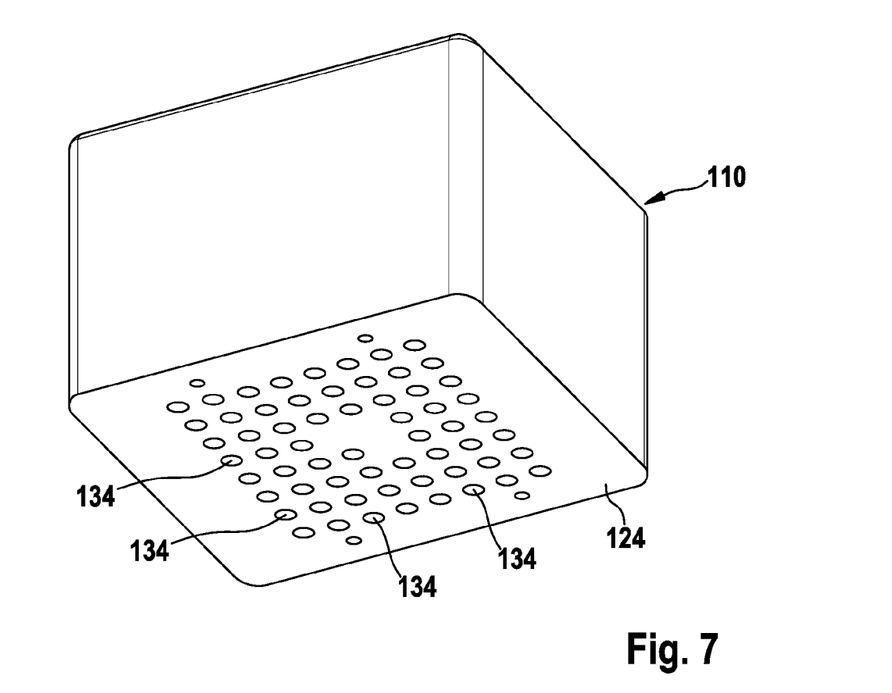
FIG. 7 shows schematically and exemplary a representation of a bottom view of an embodiment the shielding device of the present invention and
   FIG. 8 shows exemplary a flowchart illustrating an embodiment of the method of the third aspect of the invention.

FIG. 7 shows schematically and exemplary a bottom view of the shielding device in an assembled state. As can be seen, the electronic component is completely sheathed by the shielding device.

The plurality of landing pads 134 arranged at a bottom surface of the lower insulating layer 124 of the bottom shielding serve for electrically connecting the electronic component shielded by the shielding device to other components. Additionally the quantity and/or size of these pads can be increased to enhance the mechanical strength of the attachment of the device to the printed circuit board.

Figure 8:
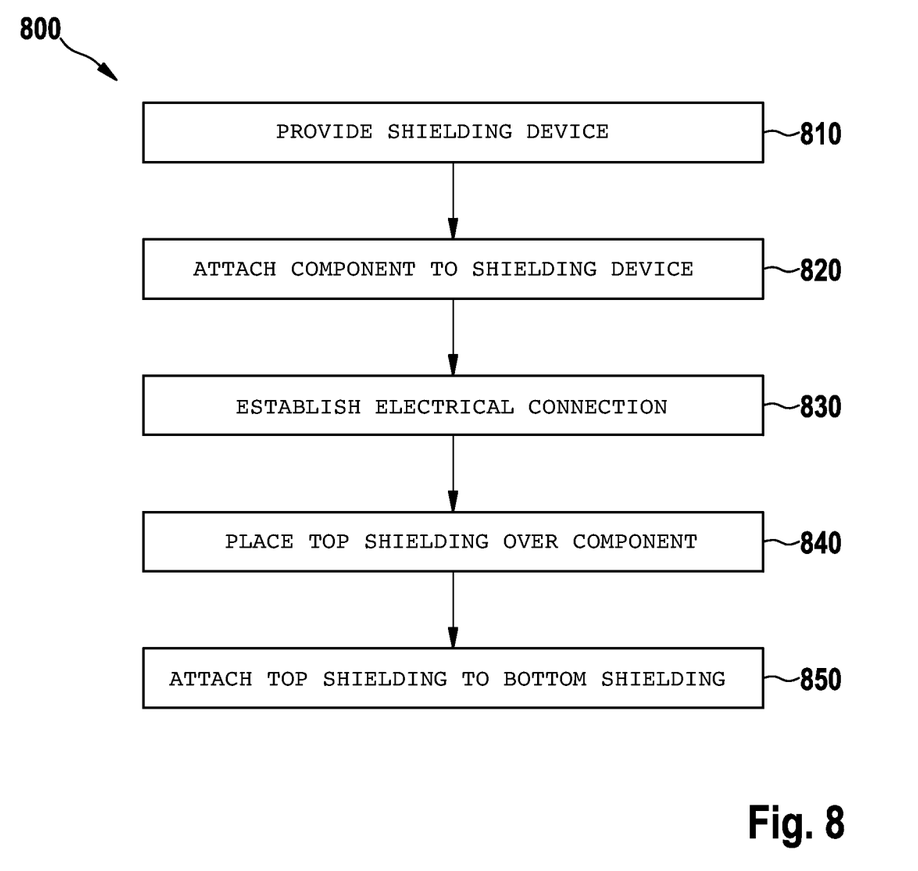

FIG. 8 shows exemplary a flow chart 800 illustrating an embodiment of the method of the third aspect of the invention. In a first step 810, a shielding device according to the first aspect of the invention is provided. In a second step 820, the electronic component to be shielded is attached to a top surface of a bottom shielding of the shielding device.

In a third step 830, an electronic connection between the electronic component and transmission lines of the shielding device is established, for instance through soldering. In a fourth step 840, a top shielding which is usually five-sided, is imposed over the electronic component. In this step, it is ensured that the top shielding is in contact with electrically and/or magnetically conductive sheet layer/layers of the bottom shielding. In a fifth step 850, the top shielding is attached to the bottom shielding such that the shielding device completely envelopes the electronic component.

The disclosed examples and embodiments are presented for purposes of illustration only. Other alternate embodiments may include some or all of the features disclosed herein. Although an exemplary embodiment of one or more embodiments of the invention has been shown and described, it should be apparent to those of ordinary skill that a number of changes and modifications may be made without departing from the spirit and scope of the invention. Embodiments of the invention can readily be adapted to a number of different kinds of shielding devices by following the present teachings. All such changes, modifications and alterations should therefore be recognized as falling within the scope of one or more embodiments of the invention.

LIST OF REFERENCES 1 attachment pins of a prior art transformer
2 magnetic core of a prior art transformer
3 bobbin of a prior art transformer
4 isolation wraps of a prior art transformer
12 top part of a prior art shielding cap
14 bottom part of a prior art shielding cap
16 cutouts of a bottom part of a prior art shielding cap
100 first embodiment of the shielding device
102 electronic component
104 attachment pins of the electronic component
110 top shielding
112 bottom edges of the top shielding
120 bottom shielding of the first embodiment
122 electrically and/or magnetically conductive metal sheet layer
124 lower insulating layer
126 middle insulating layer
128 upper insulating layer
130 plurality of connection pads
132 printed circuit board
134 plurality of landing pads
136 plurality of transmission lines
140 bottom shielding of the second embodiment
160 bottom shielding of the third embodiment
162 first electrically and/or magnetically conductive metal sheet layer
164 second electrically and/or magnetically conductive metal sheet layer
166 first insulating sublayer
168 second insulating sublayer
172 first section of a transmission line
174 electrically conductive trace
176 second section of a transmission line
180 bottom shielding of the fourth embodiment
200 second embodiment of the shielding device
400 fourth embodiment of the shielding device

What is claimed is:

1. A shielding device configured to shield an electronic component to be mounted on a printed circuit board comprising:
   a top shielding;
   a bottom shielding;
      wherein said top shielding and said bottom shielding are configured to attach to each other and wherein said top shielding and said bottom shielding are separable from each other;
      wherein said top shielding comprises an electrically and/or magnetically conductive material;
      wherein said bottom shielding is multilayered and comprises
         at least one electrically and/or magnetically conductive metal sheet layer embedded between at least two insulating layers and comprising at least two electrically conductive transmission lines configured to conduct electric current to an electronic component, wherein the top shielding and the at least one electrically and/or magnetically conductive metal sheet layer are electrically isolated from the electronic component;
      a middle insulating layer arranged beneath the at least one electrically and/or magnetically conductive metal sheet layer; wherein said bottom shielding is integrated into the printed circuit board;
      wherein the top shielding and the bottom shielding completely envelope the electronic component when attached to each other;
      wherein the at least two electrically conductive transmission lines of the bottom shielding are each formed by at least two line sections that are displaced by a displacement from each other so that each of the at least two electrically conductive transmission lines do not form a straight line;
      wherein the middle insulating layer of the bottom shielding that is multilayered comprises a first insulating sublayer and a second insulating sublayer, the second insulating sublayer comprising a plurality of electrically conductive traces that each connect respective first and the second line sections of the at least two electrically conductive transmission lines with each other to form said displacement; and
      a gap located between said top shielding and said bottom shielding, wherein said gap comprises a width substantially equal to a thickness of at least one of said at least two insulating layers.

2. The shielding device according to claim 1, wherein at least one edge of the at least one electrically and/or magnetically conductive metal sheet layer that is exposed, such that when the top shielding and the bottom shielding are attached to each other, the top shielding contacts the at least one edge of the at least one electrically and/or magnetically conductive metal sheet layer.

3. The shielding device according to claim 1, wherein the bottom shielding that is multilayered further comprises:
   an upper insulating connection layer comprising a plurality of connection pads configured to electrically connect the electronic component;
   a first electrically and/or magnetically conductive metal sheet layer arranged beneath the upper insulating connection layer;
   the middle insulating layer arranged beneath the first electrically and/or magnetically conductive metal sheet layer;
   a second electrically and/or magnetically conductive metal sheet layer arranged beneath the middle insulating layer; and,
   a lower insulating connection layer comprising a plurality of landing pads configured to electrically connect the electronic component and arranged beneath the second electrically and/or magnetically conductive metal sheet layer, wherein each one of the plurality of landing pads is configured to connect to one of the plurality of connection pads (130) through one of said at least two electrically conductive transmission lines respectively.

4. The shielding device according to claim 1, wherein the top shielding and the bottom shielding are configured to shield the electronic component from static magnetic fields.

5. The shielding device according to claim 1, wherein the metal sheet layer/layers of the bottom shielding and the top shielding are made of a soft magnetic material.

6. The shielding device according to claim 1, wherein the metal sheet layer/layers of the bottom shielding and the top shielding are made of permalloy.

7. The shielding device according claim 1, wherein the at least one electrically and/or magnetically conductive metal sheet layer has a thickness of between 250 µm to 1 mm.

8. The shielding device according to claim 1 coupled to an electrically driven implant.

9. The shielding device according to claim 1, wherein said width of said gap is less than 100 um.

10. The shielding device according to claim 3, wherein one of the plurality of connection pads is connected to more than one of the plurality of landing pads.

11. The shielding device according to claim 3, wherein one of the connection pads is connected to more than one of the landing pads; and
wherein said middle insulating layer of the bottom shielding that is multilayered comprises a first insulating sublayer and a second insulating sublayer, the second insulating sublayer comprising a plurality of electrically conductive traces that each connect respective first and the second line sections of the at least two electrically conductive transmission lines with each other to form said displacement.

12. The shielding device according to claim 3, wherein the second electrically and/or magnetically conductive metal sheet layer exhibits a larger surface area compared to the other layers of the bottom shielding, such that the second electrically and/or magnetically conductive metal sheet layer has a protrusion area to which the top shielding can be mounted.

13. The shielding device according to claim 3, wherein said upper insulating layer comprises a plurality of corners and wherein each of said plurality of connection pads are arranged on a respective corner of said plurality of corners of said upper insulating layer.

14. A method of shielding an electronic component to be mounted on a printed circuit board, the method comprising steps of
obtaining a shielding device comprising
a top shielding;
a bottom shielding;
wherein said top shielding and said bottom shielding are configured to attach to each other and wherein said top shielding and said bottom shielding are separable from each other;
wherein said top shielding comprises an electrically and/or magnetically conductive material;
wherein said bottom shielding is multilayered and comprises
at least one electrically and/or magnetically conductive metal sheet layer embedded between at least two insulating layers and comprising at least two electrically conductive transmission lines configured to conduct electric current to an electronic component, wherein the top shielding and the at least one electrically and/or magnetically conductive metal sheet layer are electrically isolated from the electronic component;
a middle insulating layer arranged beneath the at least one electrically and/or magnetically conductive metal sheet layer;
wherein said bottom shielding is integrated into the printed circuit board;
wherein the top shielding and the bottom shielding completely envelope the electronic component when attached to each other;
wherein the at least two electrically conductive transmission lines of the bottom shielding are each formed by at least two line sections that are displaced by a displacement from each other so that each of the at least two electrically conductive transmission lines do not form a straight line; and,
wherein the middle insulating layer of the bottom shielding that is multilayered comprises a first insulating sublayer and a second insulating sublayer, the second insulating sublayer comprising a plurality of electrically conductive traces that each connect respective first and the second line sections of the at least two electrically conductive transmission lines with each other to form said displacement;
a gap located between said top shielding and said bottom shielding, wherein said gap comprises a width substantially equal to a thickness of at least one of said at least two insulating layers;
attaching the electronic component to an upper insulating layer of the bottom shielding of the shielding device;
establishing an electronic connection between the electronic component and the at least two electrically conductive transmission lines of the shielding device;
placing the top shielding of the shielding device over the electronic component, and ensuring that the top shielding is in contact with the at least one electrically and/or magnetically conductive metal sheet layer of the bottom shielding; and, attaching the too shielding to the bottom shielding.

15. The method according to claim 14, further comprising attaching the electronic component to the top surface of the bottom shielding through soldering or welding or using conductively filled adhesives.

16. The method according to claim 14, wherein at least one edge of the at least one electrically and/or magnetically conductive metal sheet layer that is exposed, such that when the top shielding and the bottom shielding are attached to each other, the top shielding contacts the at least one edge of the at least one electrically and/or magnetically conductive metal sheet layer.

17. The method according to claim 14, wherein the bottom shielding that is multilayered further comprises:
an upper insulating connection layer comprising a plurality of connection pads configured to electrically connect the electronic component;
a first electrically and/or magnetically conductive metal sheet layer arranged beneath the upper insulating connection layer;
the middle insulating layer arranged beneath the first electrically and/or magnetically conductive metal sheet layer;
a second electrically and/or magnetically conductive metal sheet layer arranged beneath the middle insulating layer; and,
a lower insulating connection layer comprising a plurality of landing pads configured to electrically connect the electronic component and arranged beneath the second electrically and/or magnetically conductive metal sheet layer, wherein each one of the plurality of landing pads is configured to connect to one of the plurality of connection pads (130) through one of said at least two electrically conductive transmission lines respectively.

18. The method according to claim 17, wherein one of the connection pads is connected to more than one of the landing pads; and wherein said middle insulating layer of the bottom shielding that is multilayered comprises a first insulating sublayer and a second insulating sublayer, the second insulating sublayer comprising a plurality of electrically conductive traces that each connect respective first and the second line sections of the at least two electrically conductive transmission lines with each other to form said displacement.

19. The method according to claim 17, wherein the second electrically and/or magnetically conductive metal sheet layer exhibits a larger surface area compared to the other layers of the bottom shielding, such that the second electrically and/or magnetically conductive metal sheet layer has a protrusion area to which the top shielding can be mounted.

* * * * *